(12) United States Patent
Horstmann et al.

(10) Patent No.: US 7,640,816 B2
(45) Date of Patent: Jan. 5, 2010

(54) MONITORING SYSTEM FOR COLLECTING AND/OR TRANSDERMALLY REDIFFUSING AIR CONTAINING ENVIRONMENTAL CONTAMINANTS, AND CORRESPONDING METHOD

(75) Inventors: Michael Horstmann, Andernach (DE); Christina Schütz, Neuwied (DE); Mohammad Sameti, Bonn (DE); Yves-Thorsten Przybylla, Nickenich (DE); Christoph Schmitz, Rheinbrohl (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 12 days.

(21) Appl. No.: 11/659,072

(22) PCT Filed: Aug. 6, 2005

(86) PCT No.: PCT/EP2005/008555

§ 371 (c)(1),
(2), (4) Date: Jan. 31, 2007

(87) PCT Pub. No.: WO2006/018166

PCT Pub. Date: Feb. 23, 2006

(65) Prior Publication Data

US 2007/0289360 A1     Dec. 20, 2007

(30) Foreign Application Priority Data

Aug. 14, 2004   (DE) ...................... 10 2004 039 570

(51) Int. Cl.
*G01N 1/22* (2006.01)

(52) U.S. Cl. .................................. 73/863.21

(58) Field of Classification Search ............... 73/23.25, 73/31.05, 863.21; 422/57, 68.1, 100; 428/173
See application file for complete search history.

(56) References Cited

U.S. PATENT DOCUMENTS

| | | | | |
|---|---|---|---|---|
| 3,552,929 A | * | 1/1971 | Field et al. | 422/56 |
| 4,092,119 A | | 5/1978 | Baier et al. | |
| 4,327,575 A | * | 5/1982 | Locker | 73/31.02 |
| 4,341,207 A | * | 7/1982 | Steer et al. | 602/56 |
| 4,595,011 A | * | 6/1986 | Phillips | 600/362 |
| 4,787,888 A | * | 11/1988 | Fox | 604/20 |
| 5,203,327 A | | 4/1993 | Schoendorfer et al. | 128/632 |
| 5,726,068 A | | 3/1998 | Rivin et al. | 436/167 |
| 6,063,029 A | * | 5/2000 | Saita et al. | 600/309 |
| 6,169,915 B1 | * | 1/2001 | Krumbiegel et al. | 600/372 |
| 2003/0194817 A1 | | 10/2003 | Glynn | 436/181 |
| 2003/0225362 A1 | | 12/2003 | Currie et al. | 604/20 |
| 2005/0002997 A1 | * | 1/2005 | Howard et al. | 424/449 |
| 2008/0092638 A1 | * | 4/2008 | Brenneman et al. | 73/61.41 |

FOREIGN PATENT DOCUMENTS

WO   WO 99/13336 A1   3/1999
WO   WO 00/03226      1/2000

* cited by examiner

*Primary Examiner*—Hezron Williams
*Assistant Examiner*—Alex Devito
(74) *Attorney, Agent, or Firm*—ProPat, L.L.C.

(57) ABSTRACT

Disclosed is a monitoring system for collecting and/or transdermally rediffusing air containing environmental contaminants. The inventive monitoring system generally includes at least one diffusion collector and/or an equilibrium diffuser. The diffusion collector is provided with at least three layers, i.e. an adhesive layer that is in direct contact with the skin of a living being, a barrier layer, and a collecting layer on the exterior face of the monitoring system. The equilibrium diffuser includes an adhesive layer and a collecting layer. The collecting layers and the adhesive layers of the two components of the monitoring system are preferably made of the same material and have the same dimensions.

19 Claims, 5 Drawing Sheets

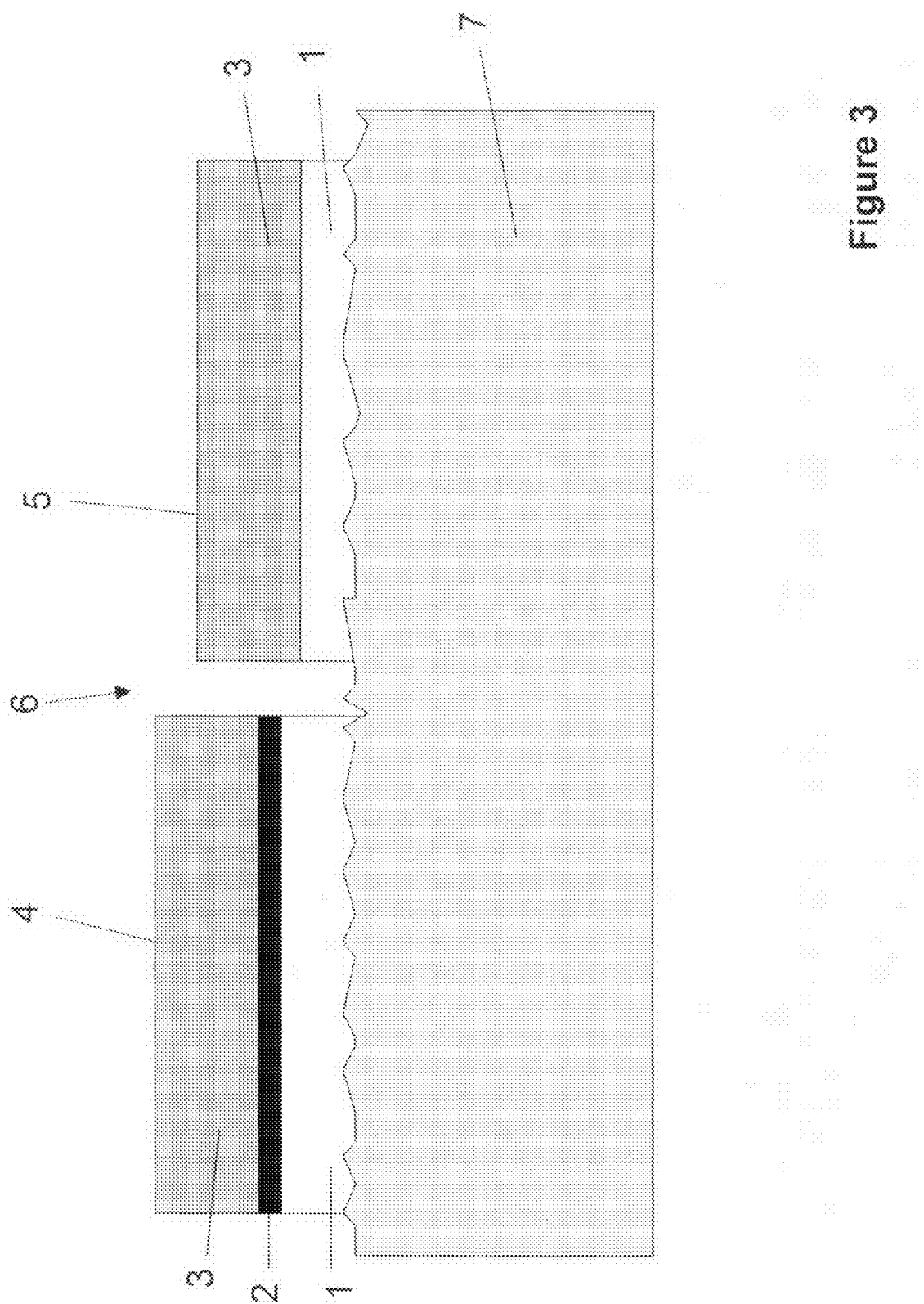

MONITORING SYSTEM FOR COLLECTING AND/OR TRANSDERMALLY REDIFFUSING AIR CONTAINING ENVIRONMENTAL CONTAMINANTS, AND CORRESPONDING METHOD

CROSS-REFERENCE TO RELATED APPLICATIONS

This application is being filed under Rule 1.371 as a National Stage Application of pending International Application No. PCT/EP2005/008555 filed Aug. 6, 2005, which claims priority to the following parent application: German Patent Application No. 10 2004 039 570.5, filed Aug. 14, 2004. Both International Application No. PCT/EP2005/008555 and German Patent Application No. 10 2004 039 570.5 are hereby incorporated by reference herein in their entirety.

FIELD OF THE INVENTION

The present invention relates to a monitoring system for collecting and/or transdermally rediffusing air containing environmental contaminants, and to a method suitable for this purpose.

BACKGROUND OF THE INVENTION

The human body is exposed to a huge number of environmental contaminants. In this connection, organic substances of high volatility also play a role in particular, because they are released by various industrial and commerical processes in which industrial waste gases, automobile exhaust gases, and solvents Used in paints are released, and because they are present everywhere and are difficult to assess in terms of the effects they have. The same applies also to the dermal uptake of cigarette smoke, all kinds of sprays and suchlike from the ambient air.

Classical methods for analysis of air contaminants use, in particular, test tubes, for example manufactured by Dräger-Werke AG, Lübeck, Germany. These test tubes are generally made of absorbent material that contains color reagents and that shows concentration-dependent visible results concerning the concentration of certain gases and volatile substances. However, such test tubes are limited to individual substances and generally have a relatively low sensitivity because the reactions have a purely chemical basis. Moreover, they only indicate the concentration measured instantaneously, and not an exposure averaged out over a certain time interval. For an exact measurement of the concentrations in the air, it is also necessary for a defined amount of air to be sucked through the test tube, and this requires extensive test apparatus.

These systems have been overtaken by what are known as diffusion monitors which are already commercially available (manufacturer 3M) and which are relatively small and can be worn on the body. Such monitors contain approximately 180 g of activated charcoal in a Teflon matrix. These appliances are suitable for determining a number of organic compounds, for example acetone, chloroform, hexane, styrene, etc. The appliances are worn on the body as capsules with a clip and are analytically evaluated after they have been worn for a period of several hours. The measurement is done by organic extraction, for example by carbon disulfide. Disadvantages of this technique are that the analysis requires the use of solvents, and a difficult manual evaluation step is therefore needed. Such diffusion collectors cannot differentiate between inhalation of contaminants and dermal uptake of contaminants.

For dermal uptake of contaminants, formulations are required that are flat and can be worn on the skin. Such diffusion collectors to be worn on the skin have not previously been disclosed.

US 2003/0225362 A1 discloses a system and a method for transdermal collection of volatile substances. For this purpose, at least one collecting device is provided for retention and diffusion of an analysis sample obtained transdermally from a person's skin, and a detector system is provided for identifying and quantifying the analysis sample. The input data of the detector system are received by a logic module and stored, and they are compared to further data concerning the person and displayed as output information which is forwarded to another system and controls the operation of the collecting device and of the detector system.

WO99/13336 relates to a noninvasive transdermal system for detection of an analysis sample extracted from an interstitial fluid in or beneath a person's skin. The system comprises a dry chemistry component which interacts with the analysis sample and has a detection sensitivity allowing it to determine the analysis sample extracted from the interstitial fluid, and a wet chemistry component for transferring the analysis sample from the interstitial fluid in or beneath the skin to the dry chemistry component in a sufficient amount that the dry component can test the analysis sample.

U.S. Pat. No. 4,092,119 describes an environmental quality indicator comprising a polymer support layer onto which a color layer is applied as indicator, said color layer changing color under the effect of certain environmental contaminants. No diffusion or permeation processes take place in the support layer. The color layer does not constitute a barrier layer, it only provides a color change caused by chemical reactions of the indicator with certain environmental contaminants.

U.S. Pat. No. 5,203,327 discloses a system with which one or more predefined analytes can be determined in the fluid released through the skin. The fluids excreted through the skin by a person can thus be analyzed for the presence of certain substances. The system comprises a gauze layer which lies on the skin, and also a porous layer, a binder layer containing a chemically or biochemically active material for binding the volatile analyte, a gas-permeable filter, and a barrier layer that protects the system against contamination from the ambient air.

In this system known from the prior art, the fluids excreted through the skin by a person are analyzed for the presence of certain substances.

SUMMARY OF ADVANTAGEOUS EMBODIMENTS OF THE INVENTION

The object of the invention is to make available a monitoring system with which certain highly volatile substances, especially contaminants, that are contained in the ambient air, can easily be collected and/or diffuse transdermally.

This object is achieved by a monitoring system which is arranged flat on the skin of a living being and has a diffusion collector composed of at least three layers and/or an equilibrium diffuser composed of at least two layers.

In one embodiment of the invention, the layer of the diffusion collector directed toward the skin of a living being is able to adhere to the skin, a barrier layer prevents diffusion of the environmental contaminants into the skin, and a collecting layer that takes up the environmental contaminants is arranged on the exterior face of the monitoring system.

In a further embodiment of the invention, the layer of the equilibrium diffuser bearing on the skin of a living being is able to adhere to the skin, and a collecting layer that takes up the environmental contaminants and permits transdermal rediffusion is located on the exterior face of the monitoring system.

Preferably, the collecting layer is composed of at least one polymer material suitable for transdermal purposes. Porous, absorbent materials are added to the polymer material(s) in order to increase the solubility and the absorption of organic environmental contaminants.

The polymer material(s) can expediently be chosen from the group comprising silicone copolymers, polyisobutylene, acrylate copolymers, and styrene-isoprene copolymers. The porous, absorbent materials are preferably chosen from the group comprising activated charcoal, bentonite, silicon dioxide, and synthesized polymers with specific affinities for certain organic trace elements.

The further design of the monitoring system will be clear from the features of patent claims 8 through 16.

The present object is also to provide a method for collecting and for monitoring the dermal uptake of environmental contaminants, said method comprising the following method steps:

(a) planar application, to the skin, of a first polymer material which is suitable for transdermal purposes and contains porous, absorbent materials for the uptake of environmental contaminants, permitting an uptake of environmental contaminants from the material into the skin,
(b) planar application of a further polymer material of the same type to the skin, with a barrier layer screening the material off from the skin,
(c) exposure of the two polymer materials to the ambient air for the same length of time and removal of the materials from the skin before the onset of the uptake saturation of the materials for the environmental contaminants, and
(d) analytical determination of the individual environmental contaminants in the first polymer material and in the further polymer material.

For the analytical determination, the environmental contaminants are preferably extracted from the two polymer materials by means of organic solvents, and the solutions obtained are compared with standard solutions by means of chromatography in order to determine the amounts of environmental contaminants taken up by the materials.

In one embodiment of the method, each of the two polymer materials, after exposure, is positioned in a closed vessel that is heated in a headspace gas chromatograph, with a state of equilibrium being established between the environmental contaminants diffusing from the materials into a gas space in the respective vessel and the environmental contaminants remaining in the material, and the amounts of the environmental contaminants are measured from the gaseous phase of the gas space. By comparing the measured amounts and concentrations of the environmental contaminants in the two polymer materials, an estimated value for the rate of dermal delivery of environmental contaminants to a living being is determined.

The invention affords the advantage that the monitoring system comprises a diffusion collector and equilibrium diffuser which can be used jointly, or each component can be used on its own. In the combined use of diffusion collector and equilibrium diffuser, a particularly simple and reliable assessment of the rate of transdermal uptake of the environmental contaminants is possible. When the diffusion collector and the equilibrium diffuser are used independently of one another, the analysis of the contaminants retained in the diffusion collector allows conclusions to be drawn regarding the concentrations of the individual substances and which substances are present in the ambient air. If the equilibrium diffuser is used on its own, the measurement of the environmental contaminants present in the equilibrium diffuser allows conclusions to be drawn regarding the transdermal uptake of the environmental contaminants in relation to their concentrations and amounts.

BRIEF DESCRIPTION OF THE DRAWINGS

The invention is explained in more detail below on the basis of illustrative embodiments depicted in the drawing, in which:

FIG. 3 shows the planar arrangement of a monitoring system according to the invention on the skin of a living being.

DETAILED DESCRIPTION OF ADVANTAGEOUS EMBODIMENTS OF THE INVENTION

The monitoring system 6 according to the invention comprises a polymer-containing transdermal planar formulation that is affixed to the skin of a living being and, after being worn for a period of several hours, possibly for up to 24 hours, is evaluated by analytical determination of the trace amount of organic volatile compounds that has been taken up via the air.

The monitoring system 6 (see FIGS. 3, 4*a* and 4*b*) comprises at least a diffusion collector 4, 8 and/or at least an equilibrium diffuser 5. Depending on the measurements that are to be carried out, it can comprise only the air contamination diffusion collector 4, 8 to be worn on the skin, but also collection systems of the type which, in addition to the diffusion collectors, comprise the same number of equilibrium diffusers 5 as storage devices for organic trace elements and which at the same time permit rediffusion of the trace elements into the skin.

Figure 1:
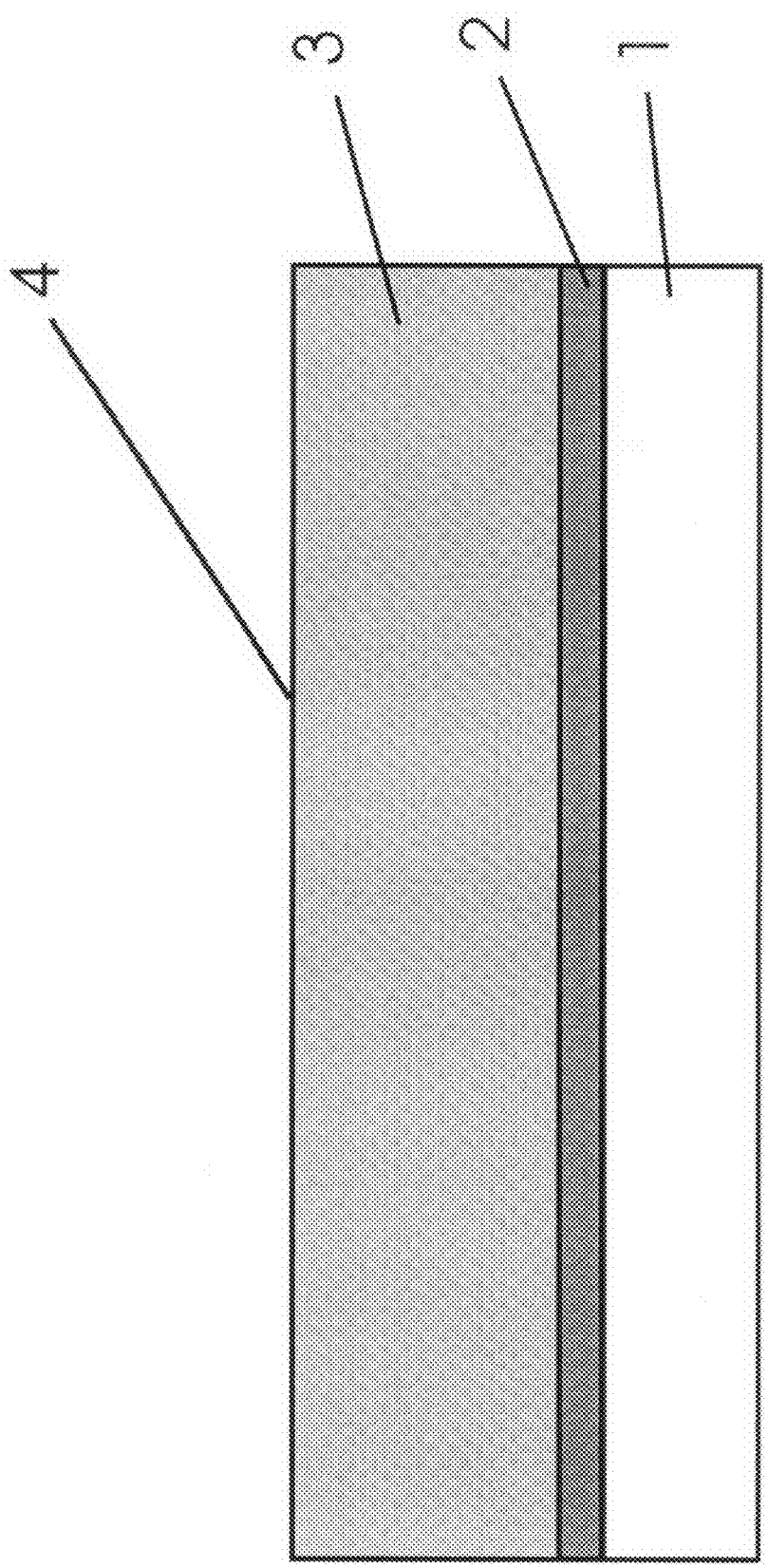
FIG. 1 shows a schematic cross section through a diffusion collector according to the invention.

FIG. 1 shows a schematic cross section through a diffusion collector 4 composed of at least three layers, namely an adhesive layer 1 directed toward the skin, a barrier layer 2 preventing diffusion, and a collecting layer 3 arranged on the exterior face of the monitoring system.

The composition of the collecting layer 3 can be adapted to the particular application purpose. The texture of the collecting layer 3 is sufficiently stiff to be worn for a 24-hour period. For this application, polymer materials are fundamentally suitable as the main component. Because of their good compatibility with the skin, materials that are particularly well suited are silicone copolymers, polyisobutylene, styrene-isoprene copolymers, and other materials used for transdermal therapeutic systems. To increase the solubility and the absorption of organic contaminants, porous and absorbent materials such as activated charcoal, bentonite, and silicon dioxide are added to the polymer materials. Synthesized polymers are used especially for the absorption of certain individual substances. The technique of preparing such synthesized polymers with special affinity for trace elements is to be found described in detail in the literature under the term "molecular imprinting".

The adhesive layer 1 of the diffusion collector 4 is made, for example, of biocompatible adhesive polymers, with silicone polymers being the material of first choice here. In addition, polyacrylates and isobutylene are also suitable adhesives. Preferred layer thicknesses of the collecting layer 3 are between 1 and 100 μm. The adhesive layer has a thickness of between 5 and 200 μm. The thickness is preferably between 5 and 100 μm. For the choice of the barrier layer 2, all raw materials are suitable that are flexible and allow no diffusion or only minimal diffusion of various contaminants. Particular preference is given here to pure metals such as aluminum, silver and gold, which are used in thin layers of approximately 1 to 5 μm in thickness. Ideally, the metals should be present in elemental form as a film. It is also possible to perform vapor-deposition of the underside of the collecting layer 3 shown in FIG. 1 in a vacuum with one of said metals. Polymers such as polytetrafluoroethylene, polyethylene terephthalate or acrylonitrile copolymers are also highly suitable as barrier layers.

Figure 2:
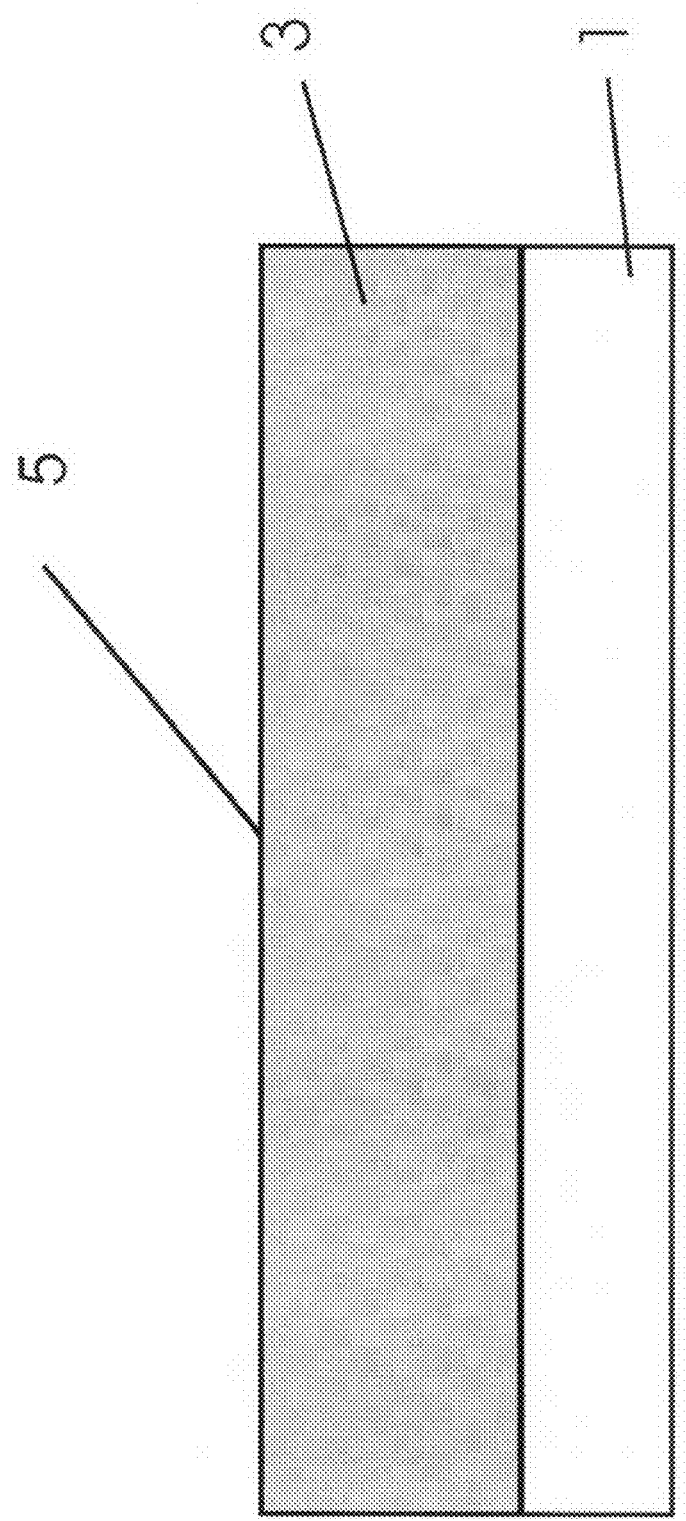
FIG. 2 shows a schematic cross-sectional view through an equilibrium diffuser according to the invention.

The structure of the equilibrium diffuser 5 differs from that of the diffusion collector 4 through the absence of the barrier layer 2, as can be seen in FIG. 2. The adhesive layer 1 and the collecting layer 3 of an equilibrium diffuser 5 are preferably identical to the corresponding layers 1 and 3 of a diffusion collector 4. In other words, the diffusion collector 4 and the equilibrium diffuser 5 each have adhesive layers 1 and collecting layers 3 of the same material. In addition, the collecting layers 3 and the adhesive layers 1 of diffusion collector 4 and equilibrium diffuser 5 have the same dimensions. Both the diffusion collector 4 and the equilibrium diffuser 5 can contain one or more additional layers as barrier layers for certain environmental contaminants, and as nonstick layers for textiles, plastics, leather and suchlike. The additional barrier layers allow the monitoring system to be designed only for the measurement of certain substances contained in the air, since only these substances pass through the barrier layers, and the other contaminants cannot pass through these barrier layers. The nonstick layers, which are each applied on the exterior face of the collecting layers of the monitoring system, serve to prevent the collecting layers from sticking to an item of clothing made of textile or leather on the person who is wearing the monitoring system on his or her skin.

FIG. 3 shows the monitoring system 6 composed of a diffusion collector 4 and of an equilibrium diffuser 5 which both lie flat on a person's skin 7. The whole monitoring system 6 is subjected to exposure to contaminated air, i.e. the same amounts of air act on the diffusion collector 4 and on the equilibrium diffuser 5, since the dimensions and therefore the volumes of the respective collecting layers 3 and also of the adhesive layers 1 are the same. Since the materials of the layers 1 and 3 are also in each case the same in the diffusion collector 4 and the equilibrium diffuser 5, the diffusion and permeation processes through the skin can be compared with one another.

Figure 4A:
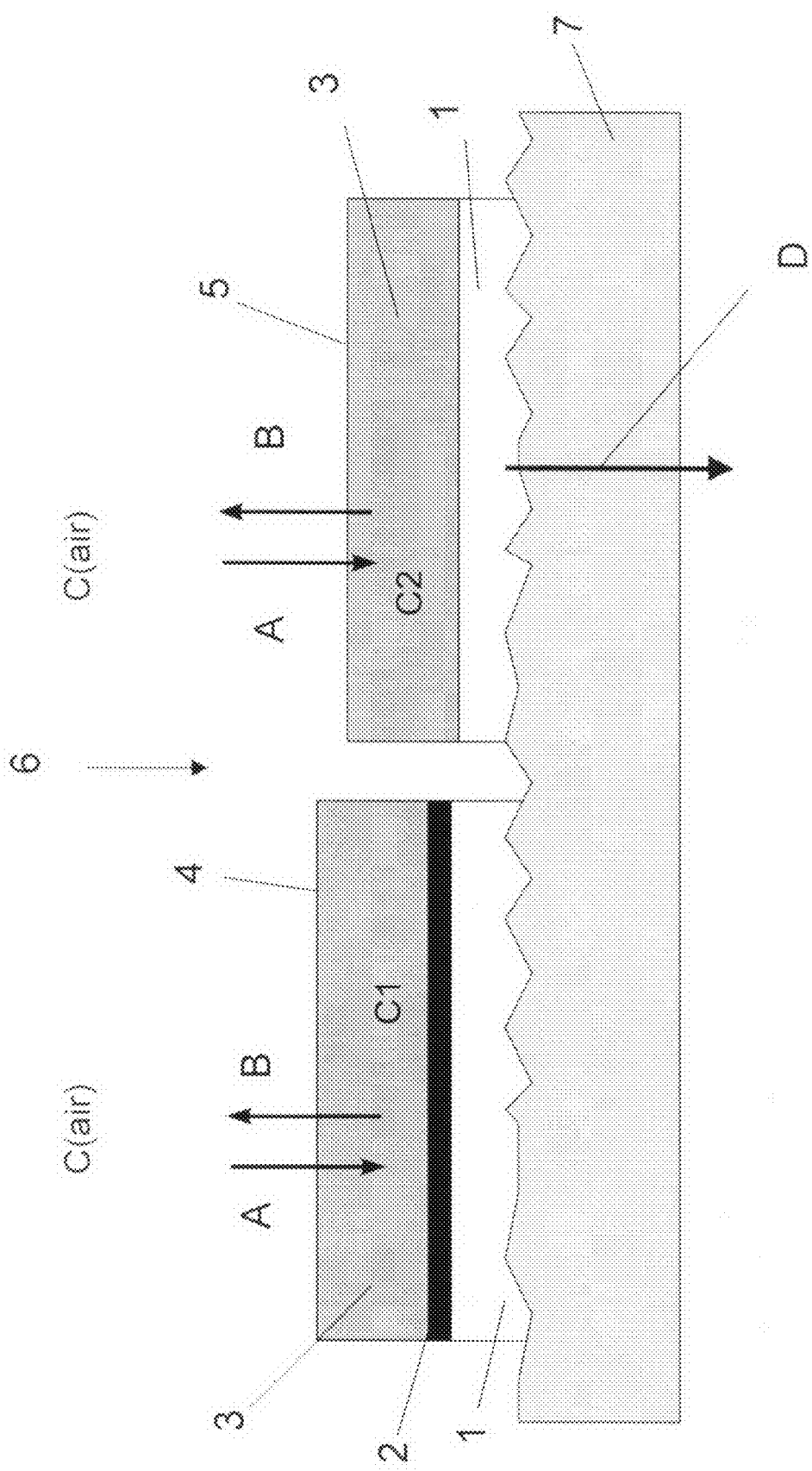
FIG. 4*a* shows a schematic representation of the diffusion ratios in the diffusion collector and in the equilibrium diffuser and, in the latter, the transdermal permeation.
Figure 4B:
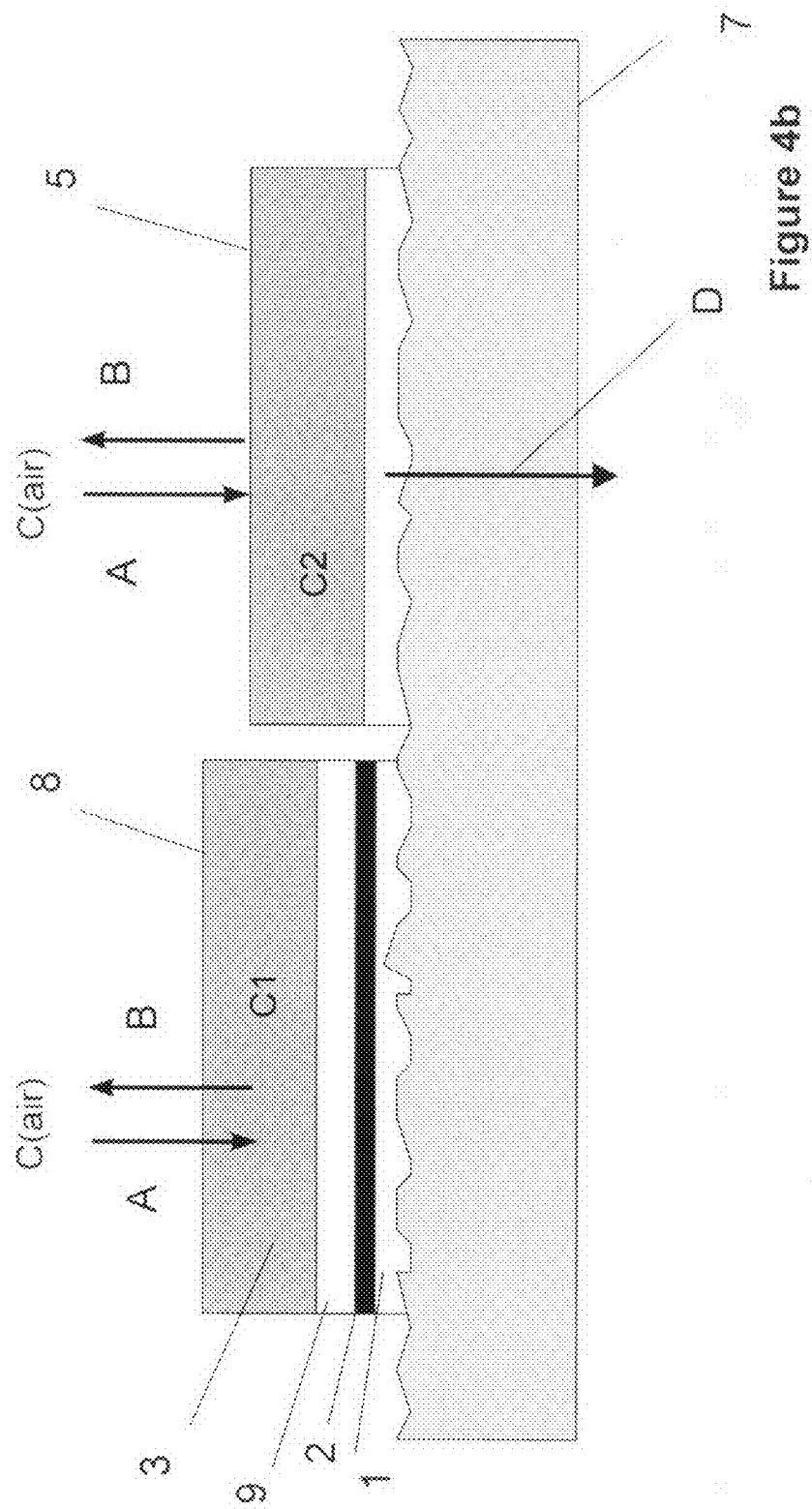
FIG. 4*b* shows a schematic representation of the diffusion ratios in a slightly modified embodiment of the diffusion collector compared to FIG. 4*a*, and in the equilibrium diffuser and, in the latter, the transdermal permeation.

In FIGS. 4a and 4b, diffusion and permeation processes in the diffusion collectors 4, 8 and in the equilibrium diffuser 5 of the monitoring system 6 are indicated. The ambient air has a concentration C of volatile contaminants. Diffusion processes, indicated by the arrows A and B, occur at the interface between the ambient air and the components of the monitoring system 6. Diffusion is understood as a movement of atoms, ions and molecules from high to low concentration within a medium. Only after uniform distribution of all the particles in a system is no net movement any longer detectable, since then a concentration balance is reached and the system is in a state of equilibrium. The speed of the particles is dependent on temperature and increases as the temperature rises. It is thus assumed that the particles move randomly, so that at first individual particles, at the start of the exposure, pass through the interface or separation surface between air and collecting layer, i.e. move in the direction of the arrow A into the collecting layer 3. Quite a lot of these particles, but not all, pass back into the air again, as is indicated by the arrow B, so that there is a net movement or a net flow of particles in the direction of the collecting layer, which was originally free of contaminants. After a certain exposure period, the aforementioned equilibrium in the system will reestablish itself and the concentration of the contaminants in the collecting layer is then C1. Since the diffusion collector 4 is equipped with a barrier layer, the collected contaminants cannot diffuse further in the direction of the skin 7. In the equilibrium diffuser 5, a rediffusion into the skin is possible, since there is no barrier layer. The diffusion processes at the interface or separation surface between ambient air and collecting layer 3 are the same as in the diffusion collector 4, provided that the materials of the two collecting layers 3 are the same and that they have the same dimensions.

Some of the contaminant particles diffusing into the collecting layer 3 in the direction of the arrow A will diffuse back again into the ambient air (see arrow B), while others will be taken up transdermally by the skin 7 via the adhesive layer 1. This permeation is indicated by the arrow D. The permeation is dependent on the permeability, which is to be understood as the diffusion of particles through surfaces (membranes). The skin 7 can be regarded as a biological membrane which does not have the same level of permeability for all substances. It is selectively permeable, i.e. the skin is permeable for a substance I, but not for a substance II. The permeability is selective and is dependent on the presence of specific carrier molecules in the skin, with an affinity to a certain group of chemically related substances.

In the equilibrium diffuser 5, an equilibrium is established with the concentration C2 of the contaminants. The concentration C2 is less than the concentration C1 in the diffusion collector 4, since some of the contaminants do not remain in the collecting layer 3 of the equilibrium diffuser 5 and instead diffuse further in the direction of the skin 7.

After the monitoring system has been worn for a certain period of time on the skin 7 of the exposed person or of the exposed animal, the monitoring system is removed from the skin. The wearing period is specific to each individual substance that is to be measured, i.e. entails a different length of time. It generally holds true that the minimum time for which the measuring system is worn, namely about 4 to 5 hours, is for the substance with the shortest saturation time for being taken up into the collecting layer 3. The other substances to be examined then have a longer wearing time than the minimum wearing time. It is therefore expedient to use a monitoring system with several diffusion collectors 4 and equilibrium diffusers 5 if a relatively large number of contaminants are to be measured. The single pair of a diffusion collector 4 and an equilibrium diffuser 5 is then designed for measuring one or a few contaminants. Each further pair of diffusion collector 4 and equilibrium diffuser 5 is prepared for measuring one or more contaminants that differ from those contaminants which are measured with the aid of the aforementioned single pair. In this way it is possible to measure a large number of different contaminants with the monitoring system.

As soon as the monitoring system has been removed from the skin, it is subjected to analytical working-up and analytical determination of the contaminants, if appropriate after an optional intermediate storage phase. The analytical working-up is carried out by known methods, for example gas chromatography. This generally entails initial extraction with an organic solvent of the greatest purity which does not contain the respective contaminating agent. The solution obtained is analyzed in a high-pressure liquid chromatograph or gas chromatograph. By comparing with known standard solutions that contain the same contaminants as in the solution to be examined, the amount of contaminants taken up by the monitoring system can be determined. In the method for collecting and for monitoring the dermal uptake of environmental contaminants from air, the procedure is as follows: at least one polymer material which is suitable for transdermal purposes, and contains porous, absorbent materials for the uptake of certain environmental contaminants, is fixed flat on the skin. A polymer material of a similar type, which has a barrier layer screening it off from the skin, is also fixed flat on the skin. The two polymer materials are exposed for the same length of time and are thereafter removed from the skin, specifically at a time before the onset of the uptake saturation of the materials for the environmental contaminants. Thereafter, the collected environmental contaminants are extracted and subjected to analytical determination.

If the materials are not removed until after the onset of the uptake saturation of the materials for the environmental contaminants, then, with the concentration C2 in the collecting layer 3 of the equilibrium diffuser 5, the permeation may also change, and therefore also the dermal delivery rate in the skin, since no contaminants can be taken up in the collecting layer 3 when saturation occurs, but the permeation from the collecting layer 3 continues. If the uptake saturation occurs in the state of equilibrium in the collecting layer 3 of the diffusion collector 4 after a certain wearing time with the concentration C1 of contaminants, this is not the case in the equilibrium diffuser 5, since, because of the permeation, the concentration C2 is less than the concentration C1 and there is no state of equilibrium.

The amount of contaminants and their dermal delivery rate to the skin can also be determined chromatographically without organic solvents. For this purpose, after the exposure, the diffusion collector 4 and the equilibrium diffuser 5 and the materials of the collecting layers 3 of these components are introduced into closed glass vessels which are heated in what is called a headspace gas chromatograph. A state of equilibrium is then established between the environmental contaminants diffusing from the materials into a gas space in the respective closed vessel and the environmental contaminants remaining in the materials. The amounts and concentration of the environmental contaminants can then be measured in the gaseous phase of the gas space. By comparing the measured amounts and concentrations of the environmental contaminants in the diffusion collector 4 and in the equilibrium diffuser 5, an estimated value can be determined for the dermal delivery rate of environmental contaminants to a person or an animal. The delivery rate corresponds to the net flow through the skin, which can be regarded as a membrane, and is calculated by the formula delivery rate=$-D/d \times (C1-C2)$. The expression D/d is the permeability constant and has the dimension [cm/s]. The variable d corresponds to the thickness of the skin and the delivery rate is the number of moles migrating through a defined surface per second. Since the concentration decreases as the distance from the surface increases, the concentration gradient $(C1-C2)/d$ has a negative value.

The slightly modified embodiment of the monitoring system according to FIG. 4b differs from the embodiment according to FIG. 4a only in terms of the diffusion collector 8. The diffusion collector 8 has a barrier layer 2 which does not adjoin the underside of the collecting layer 3 but is instead arranged at a distance from this underside. Between the collecting layer 3 and the barrier layer 2 there is a further layer 9, which, for example, is a barrier layer for a specific contaminant.

The invention claimed is:

1. A dermal uptake monitoring system for collecting and rediffusing environmental contaminants present in ambient air, wherein said monitoring system can be arranged flat on the skin of a living being and comprises at least one diffusion collector and at least one equilibrium diffuser, wherein
   (i) said diffusion collector permits rediffusion of said environmental contaminants into the ambient air and prevents diffusion of the environmental contaminants into the skin and
   (ii) said equilibrium diffuser permits both rediffusion of said environmental contaminants into the ambient air and transdermal diffusion into the skin.

2. The monitoring system as claimed in claim 1, wherein the diffusion collector comprises at least three layers, (i) a layer directed toward the skin on a living being and adhering to the skin, (ii) a barrier layer preventing diffusion of the environmental contaminants into the skin, and (iii) a collecting layer taking up the environmental contaminants.

3. The monitoring system as claimed in claim 1, wherein the equilibrium diffuser comprises at least two layers, (i) a layer bearing on the skin on a living being and adhering to the skin, and (ii) a collecting layer taking up the environmental contaminants said equilibrium diffuser permitting transdermal rediffusion of said environmental contaminants into the skin.

4. The monitoring system as claimed in claim 2, wherein the collecting layer is comprised of at least one polymer material suitable for transdermal purposes.

5. The monitoring system as claimed in claim 4, wherein said polymer material further comprises porous, absorbent materials to increase the solubility and the absorption of organic environmental contaminants.

6. The monitoring system as claimed in claim 4, wherein the polymer material(s) consists of silicone copolymers, polyisobutylene, acrylate copolymers, and/or styrene-isoprene copolymers.

7. The monitoring system as claimed in claim 5, wherein the porous, absorbent materials are selected from activated charcoal, bentonite, silicon dioxide, and/or synthesized polymers with specific affinities for certain organic trace elements.

8. The monitoring system as claimed in claim 2, wherein the adhesive layer contains silicone copolymers, polyacrylates, polyisobutylene or mixtures thereof.

9. The monitoring system as claimed in claim 2, wherein the barrier layer comprises pure metal, polyethylene terephthalate, acrylonitrile copolymer or polytetrafluoroethylene.

10. The monitoring system as claimed in claim 9, wherein the metal is aluminum, silver or gold.

11. The monitoring system as claimed in claim 2, wherein both the diffusion collector and also the equilibrium diffuser contain one or more additional layers as barrier layer(s) for certain environmental contaminants, and/or nonstick layers for textiles, plastics, or leather.

12. The monitoring system as claimed in claim 2, wherein the diffusion collector and the equilibrium diffuser each have collecting layers and adhesive layers of the same material.

13. The monitoring system as claimed in claim 2, wherein the collecting layers and the adhesive layers of the diffusion collector and the equilibrium diffuser each have the same dimensions.

14. The monitoring system as claimed in claim 2, wherein the adhesive layer has a thickness of 5 to 200 μm.

15. The monitoring system as claimed in claim 2, wherein the diffusion collector consists of a collecting layer, a barrier layer and an adhesive layer and the diffusion collector has a thickness of 7 to 305 μm.

16. The monitoring system as claimed in claim 1, wherein the living being is a human or an animal.

17. The monitoring system as claimed in claim 14, wherein the adhesive layer has a thickness of 5 to 100 μm.

18. An equilibrium diffuser for transdermally re-diffusing air contaminants comprising (i) an adhesive layer which can adhere to skin, and (ii) a collecting layer taking up air contaminants, said collecting layer comprising polymer(s) consisting of silicone copolymers, polyisobutylene, acrylate copolymers, or styrene-isoprene copolymers, wherein said equilibrium diffuser does not include a barrier layer thereby permitting transdermal rediffusion.

19. A monitoring system as claimed in claim 1, wherein said system further comprises a means for analytical determination of individual environmental contaminants within said diffusion collector and said equilibrium diffuser.

* * * * *